(12) United States Patent
Van Tol et al.

(10) Patent No.: US 11,304,719 B2
(45) Date of Patent: Apr. 19, 2022

(54) ULTRASONIC DISSECTOR AND SEALER

(71) Applicant: COVIDIEN LP, Mansfield, MA (US)

(72) Inventors: David J. Van Tol, Boulder, CO (US); Anthony B. Ross, Boulder, CO (US); Robert B. Stoddard, Steamboat Springs, CO (US)

(73) Assignee: Covidien LP, Mansfield, MA (US)

( * ) Notice: Subject to any disclaimer, the term of this patent is extended or adjusted under 35 U.S.C. 154(b) by 326 days.

(21) Appl. No.: 15/904,606

(22) Filed: Feb. 26, 2018

(65) Prior Publication Data
US 2018/0185055 A1 Jul. 5, 2018

Related U.S. Application Data

(63) Continuation of application No. 14/464,860, filed on Aug. 21, 2014, now Pat. No. 9,918,736.

(60) Provisional application No. 61/882,035, filed on Sep. 25, 2013, provisional application No. 61/882,033, filed on Sep. 25, 2013.

(51) Int. Cl.
*A61B 17/32* (2006.01)
*A61B 17/29* (2006.01)
*A61B 18/00* (2006.01)
*A61N 7/00* (2006.01)

(52) U.S. Cl.
CPC .............. *A61B 17/320092* (2013.01); *A61B 17/320068* (2013.01); *A61B 2017/2948* (2013.01); *A61B 2017/320072* (2013.01); *A61B 2017/320074* (2017.08); *A61B 2017/320075* (2017.08); *A61B 2017/320078* (2017.08); *A61B 2017/320089* (2017.08); *A61B 2017/320093* (2017.08); *A61B 2017/320094* (2017.08); *A61B 2017/320095* (2017.08); *A61B 2018/00589* (2013.01);
(Continued)

(58) Field of Classification Search
CPC .... A61B 17/320068; A61B 17/320092; A61B 2017/320072; A61B 2017/00526; A61B 2017/2948
See application file for complete search history.

(56) References Cited

U.S. PATENT DOCUMENTS 5,322,055 A 6/1994 Davison et al.
5,391,144 A 2/1995 Sakurai et al.
(Continued)

FOREIGN PATENT DOCUMENTS

DE 03507672 A1 9/1986
DE 03630478 C1 1/1988
(Continued)

OTHER PUBLICATIONS

European search report dated Jan. 22, 2015 issued in European Appln. No. 14184055.
(Continued)

*Primary Examiner* — Julie A Szpira
(74) *Attorney, Agent, or Firm* — Carter, DeLuca & Farrell LLP

(57) ABSTRACT

A method for ultrasonically treating tissue includes accessing a surgical site with an ultrasonic surgical instrument, dissecting tissue with a first portion of the blade, and sealing tissue with a second portion of the blade. The instrument includes a blade that defines a longitudinal axis. The blade is configured to oscillate along the longitudinal axis to ultrasonically treat tissue.

10 Claims, 6 Drawing Sheets

(52) U.S. Cl.
CPC .............. *A61B 2018/00601* (2013.01); *A61B 2018/00607* (2013.01); *A61N 7/00* (2013.01)

(56) References Cited

U.S. PATENT DOCUMENTS

| | | | |
|---|---|---|---|
| 5,562,693 A | 10/1996 | Devlin et al. | |
| 5,989,275 A * | 11/1999 | Estabrook | A61B 17/22012 604/22 |
| 6,051,010 A * | 4/2000 | DiMatteo | A61B 17/22012 606/169 |
| 6,117,152 A * | 9/2000 | Huitema | A61B 17/00008 606/169 |
| 6,278,218 B1 * | 8/2001 | Madan | A61B 17/320068 310/312 |
| 6,443,969 B1 * | 9/2002 | Novak | A61B 17/320068 606/169 |
| 6,454,781 B1 * | 9/2002 | Witt | A61B 17/320092 606/169 |
| 6,561,983 B2 * | 5/2003 | Cronin | B06B 3/00 600/461 |
| 6,669,690 B1 * | 12/2003 | Okada | A61B 17/320092 606/40 |
| 6,837,888 B2 | 1/2005 | Ciarrocca et al. | |
| 6,887,252 B1 * | 5/2005 | Okada | A61B 17/320092 606/169 |
| 6,976,969 B2 * | 12/2005 | Messerly | A61B 17/320092 601/2 |
| 7,780,659 B2 * | 8/2010 | Okada | A61B 17/320092 606/40 |
| 8,057,498 B2 * | 11/2011 | Robertson | A61B 17/3205 606/169 |
| 8,142,461 B2 * | 3/2012 | Houser | A61B 17/320092 606/169 |
| 8,348,967 B2 * | 1/2013 | Stulen | A61B 17/320068 606/169 |
| 8,469,981 B2 * | 6/2013 | Robertson | A61B 17/22004 606/169 |
| 9,393,037 B2 * | 7/2016 | Olson | A61B 17/22004 |
| 9,622,767 B2 | 4/2017 | Stoddard et al. | |
| 9,655,641 B2 | 5/2017 | Stoddard et al. | |
| 9,872,698 B2 | 1/2018 | Van Tol et al. | |
| 2002/0103438 A1 * | 8/2002 | Cronin | B06B 3/00 600/459 |
| 2005/0004589 A1 * | 1/2005 | Okada | A61B 17/320092 606/169 |
| 2007/0016235 A1 * | 1/2007 | Tanaka | A61B 17/320092 606/169 |
| 2007/0060926 A1 | 3/2007 | Escaf | |
| 2008/0009848 A1 * | 1/2008 | Paraschiv | A61B 17/320068 606/34 |
| 2008/0051814 A1 | 2/2008 | Beaupre | |
| 2008/0234709 A1 * | 9/2008 | Houser | A61B 17/320068 606/169 |
| 2008/0234710 A1 * | 9/2008 | Neurohr | A61B 17/320068 606/169 |
| 2008/0243106 A1 * | 10/2008 | Coe | A61B 17/00234 606/1 |
| 2008/0255451 A1 * | 10/2008 | Cohen | G01S 7/52017 600/443 |
| 2009/0030438 A1 * | 1/2009 | Stulen | A61B 17/320068 606/169 |
| 2009/0216128 A1 * | 8/2009 | Sarvazyan | A61B 8/4281 600/459 |
| 2009/0216157 A1 * | 8/2009 | Yamada | A61B 17/320092 601/2 |
| 2009/0326535 A1 * | 12/2009 | Blus | A61B 17/320068 606/80 |
| 2010/0057118 A1 * | 3/2010 | Dietz | A61B 17/320068 606/169 |
| 2010/0094321 A1 * | 4/2010 | Akahoshi | A61F 9/00745 606/169 |
| 2013/0116717 A1 * | 5/2013 | Balek | A61B 17/320068 606/169 |

FOREIGN PATENT DOCUMENTS

| | | |
|---|---|---|
| DE | 20118698 U1 | 4/2003 |
| DE | 20118699 | 4/2003 |
| DE | 20303776 U1 | 7/2004 |
| JP | 61096419 | 5/1986 |
| JP | 63302699 | 12/1988 |
| JP | 02034008 | 2/1990 |
| JP | 06114069 | 4/1994 |
| JP | 2000237204 A | 9/2000 |
| JP | 21212514 | 8/2001 |
| JP | 2001212514 A | 8/2001 |
| JP | 2001346805 A | 12/2001 |
| JP | 2002045368 A | 2/2002 |
| JP | 2002186901 A | 7/2002 |
| JP | 24254128 | 9/2004 |
| JP | 3696034 B2 | 9/2005 |
| JP | 3756726 B2 | 3/2006 |
| WO | 9314709 A1 | 8/1993 |
| WO | 2004026104 A2 | 4/2004 |
| WO | 2005122917 A1 | 12/2005 |
| WO | 2006059120 A1 | 6/2006 |
| WO | 2007014548 A2 | 2/2007 |

OTHER PUBLICATIONS

European Examination Report dated Apr. 6, 2021 issued in corresponding EP Appln. No. 14 184 055.3.

* cited by examiner

ULTRASONIC DISSECTOR AND SEALER

CROSS-REFERENCE TO RELATED APPLICATIONS

This application is a continuation of U.S. patent application Ser. No. 14/464,860, filed Aug. 21, 2014, which claims the benefit of, and priority to, U.S. Provisional Patent Application Ser. Nos. 61/882,035, filed Sep. 25, 2013, and 61/882,033, filed Sep. 25, 2013. This application is related to U.S. patent application Ser. No. 14/464,832, filed Aug. 21, 2014, now U.S. Pat. No. 9,872,968. The entire contents of each of the above applications are hereby incorporated herein by reference.

BACKGROUND

1. Technical Field

The present disclosure relates to surgical instruments and, more specifically, to ultrasonic surgical instruments having features for dissecting and sealing tissue.

2. Discussion of Related Art

Energy-based tissue treatment is well known in the art. Various types of energy (e.g., electrical, ultrasonic, microwave, cryogenic, thermal, laser, etc.) are applied to tissue to achieve a desired result. Ultrasonic energy may be delivered to tissue using a surgical probe that includes a transducer coupled with an end effector configured to deliver the ultrasonic energy to tissue.

A typical ultrasonic surgical instrument generates a sinusoidal driving signal that causes the mechanical tip of a waveguide to vibrate at a selected frequency, usually from about 20 KHz to about 60 KHz, for cutting and/or coagulating tissue. Improved cutting may result from increased tissue-to-mechanical tip contact caused by the high frequency of vibration of the mechanical tip in relation to tissue. Improved coagulation may result from heat generated by contact between the high frequency vibrations of the mechanical tip and body tissue.

Ultrasonic surgical instruments may include various waveguides configured to achieve a surgical result. An ultrasonic waveguide may be disposed at a distal end of the ultrasonic instrument. The waveguide may include an end effector having a cutting blade, shears, a hook, a ball, etc., and may also include other features such as jaws for grasping or manipulating tissue.

SUMMARY

In an aspect of the present disclosure, an ultrasonic surgical instrument includes a handle assembly, an elongated body, and a tool assembly. The elongated body extends distally from the handle assembly and defines a longitudinal axis. The elongated body includes a waveguide. The tool assembly includes a blade coupled to a distal end of the waveguide and a jaw member pivotally movable relative to the blade. The blade is configured to oscillate along the longitudinal axis. The blade may be an ultrasonic blade configured to ultrasonically treat tissue. The blade includes a proximal portion and a distal portion. The distal portion extends from the proximal portion and includes a top portion, a bottom portion, and planar side segments. The top portion is configured to seal tissue. The bottom portion includes a notch disposed on a surface thereof. The planar side segments extend between the top and bottom portion. One of the top portion, the bottom portion, or the notch is configured to dissect tissue.

In aspects of the present disclosure, the distal portion of the blade includes a planar distal tip.

In aspects of the present disclosure, the distal portion of the blade includes a pointed distal tip.

In aspects of the present disclosure, the notch is arcuate. The notch may include a vertical surface. The notch may include an arcuate surface.

In aspects of the present disclosure, the bottom portion of the ultrasonic blade includes converging planar surfaces.

In other aspects of the present disclosure, a method for ultrasonically treating tissue includes accessing a surgical site with an ultrasonic surgical instrument, dissecting tissue with a first portion of a blade, and sealing tissue with a second portion of the blade different that is different from the first portion of the blade. The instrument includes the blade that defines a longitudinal axis. The first portion may be a bottom portion of the blade. The second portion may be one of a top portion or planar side segments. Sealing the tissue may include clamping tissue between a top portion and a jaw pivotally movable relative to the blade.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
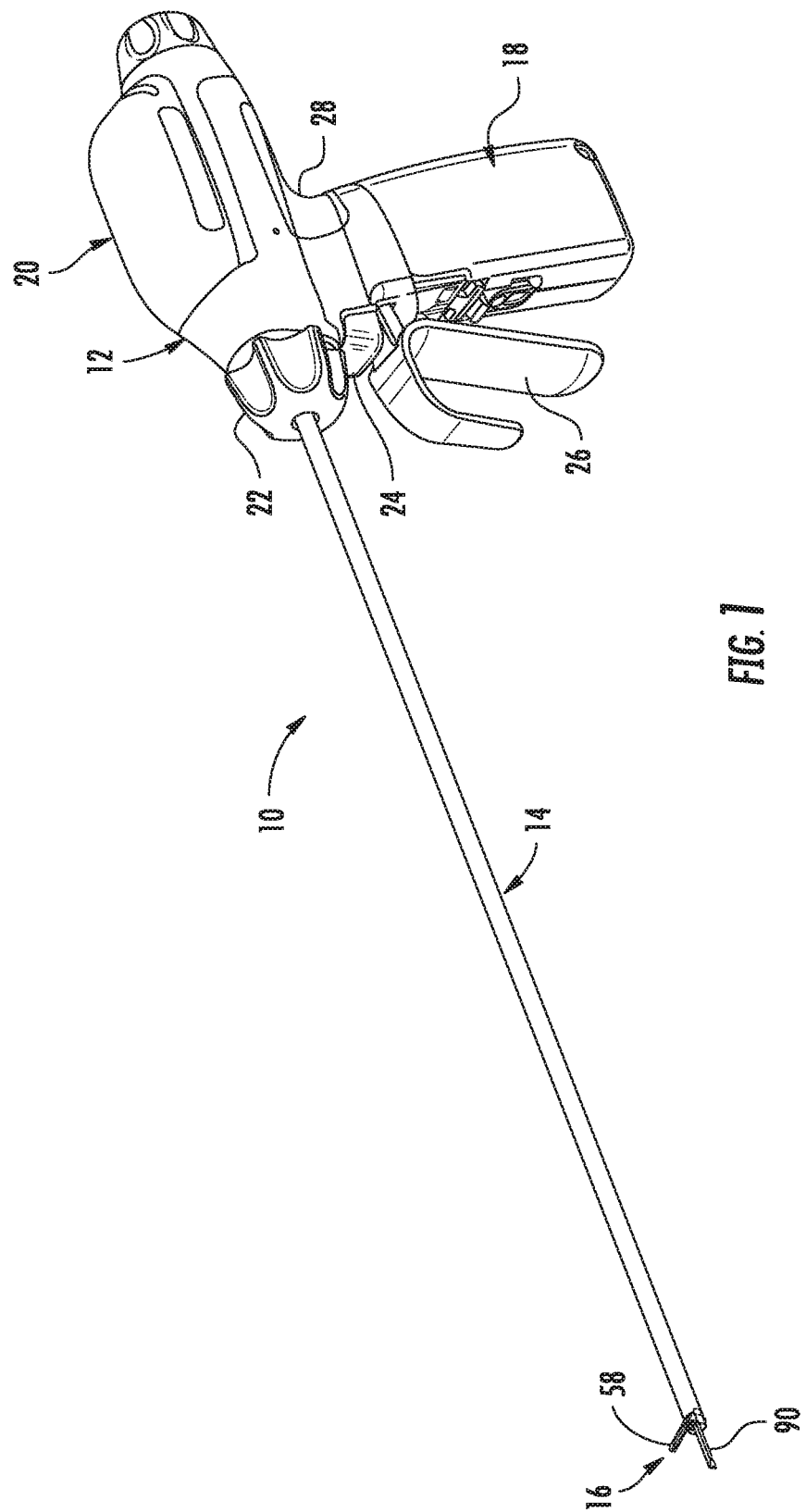
FIG. 1 is a perspective view of one illustrative embodiment of a surgical instrument provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is further from the clinician.

Referring now to FIG. 1, an ultrasonic surgical instrument 10 configured for use in accordance with the present disclosure is shown. Ultrasonic surgical instrument 10 generally includes a handle assembly 12, an elongated body portion 14, and a tool assembly 16. Handle assembly 12 supports a battery assembly 18 and an ultrasonic transducer and generator assembly (hereinafter "TAG") 20. Handle assembly 12 includes a rotatable nozzle 22, an activation button 24, and a clamp trigger 26. Battery assembly 18 and TAG 20 are each releasably secured to a central body 28 of handle assembly 12 and are removable from central body 28 to facilitate disposal of the entire device, with the exception of battery assembly 18 and TAG 20.

Figure 2:
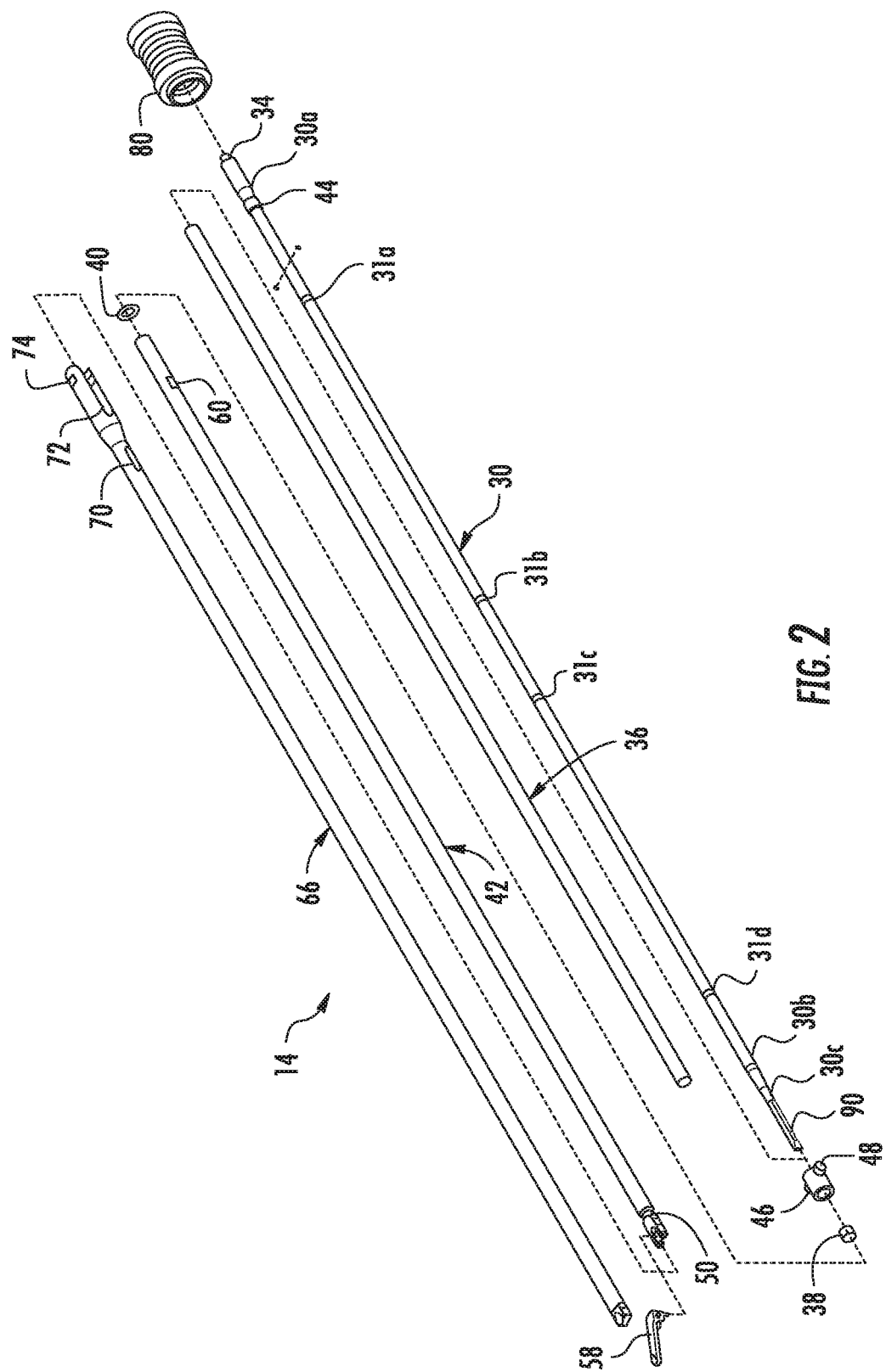
FIG. 2 is an exploded view of components of an elongated body portion of the surgical instrument of FIG. 1 in accordance with the present disclosure.

With additional reference to FIG. 2, elongated body portion 14 includes a waveguide 30 that extends from handle assembly 12 and couples tool assembly 16 (FIG. 1) thereto. A distal end of waveguide 30 defines a blade 90, which is described in further detail below. A proximal end of waveguide 30 has a threaded extension 34 for engaging TAG 20. Waveguide 30 further includes a proximal tapered portion 30a and distal tapered portions 30b and 30c. A series of annular abutments 31a-d are disposed along, e.g., machined onto, waveguide 30 at node points along waveguide 30.

An inner tube 36 is positioned about waveguide 30 between proximal tapered portion 30a and distal tapered portion 30b of waveguide 30. A distal seal member 38 is supported about waveguide 30 distally of a distal end of inner tube 36 and proximally of distal tapered portion 30c of waveguide 30 to provide a fluid-tight seal at the distal end of elongated body portion 14 between waveguide 30 and an inner surface of a middle tube 42. Ultrasonic energy is isolated from transfer to middle tube 42 by inner tube 36. A series of splines 44 are formed at the proximal end of waveguide 30. Splines 44 engage corresponding splines (not shown) formed on an inner surface of a torque adapter 46 to rotatably secure torque adapter 46 to waveguide 30. Torque adapter 46 also includes diametrically opposed wings 48 that are positioned in recesses (not shown) in rotatable nozzle 22 to secure torque adapter 46 to rotatable nozzle 22.

Figure 3:
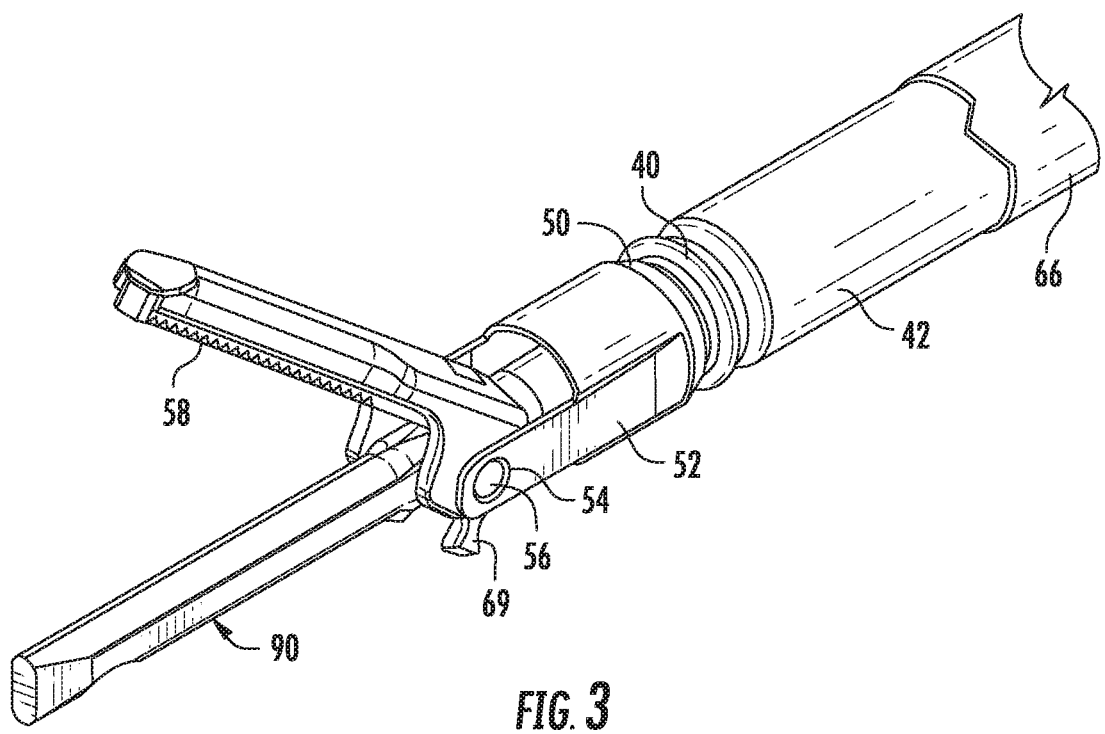
FIG. 3 is an enlarged view of a tool assembly of the surgical instrument of FIG. 1 with a portion of an outer tube of the elongated body portion of FIG. 2 cut away in accordance with the present disclosure.
Figure 4:
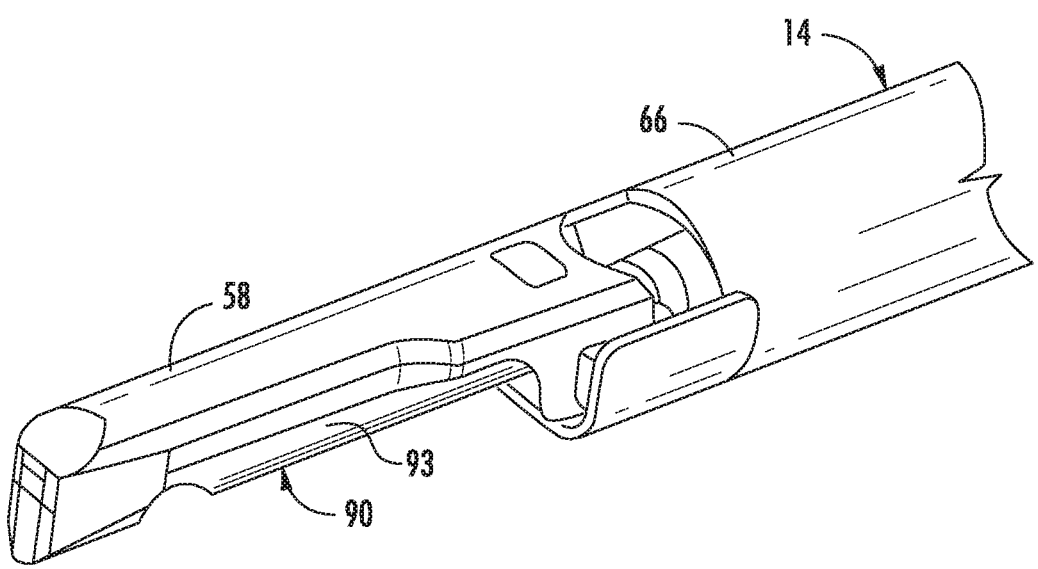
FIG. 4 is an enlarged view of the distal end of the tool assembly of FIG. 3 in the closed position in accordance with the present disclosure.

With additional reference to FIGS. 3 and 4, middle tube 42 is positioned about inner tube 36 (FIG. 2) and includes a distal end having a corset feature 50 and a pair of spaced clamp support arms 52. Corset feature 50 is positioned to receive distal seal member 38 and to maintain distal seal member 38 in the proper position about the distal end of waveguide 30. Distal seal member 38 is positioned at a node point along waveguide 30. An O-ring 40 is supported about corset feature 50 to provide a fluid-tight seal between an outer surface of middle tube 42 and an inner surface of an outer tube 66.

With reference to FIGS. 2-4, spaced clamp support arms 52 each define an opening 54 for pivotally receiving pivot members 56 formed on a clamp member 58 of tool assembly 16. Clamp member 58 of tool assembly 16 is pivotal between an open position (FIG. 3), wherein clamp member 58 is spaced from blade member 90, and a closed position (FIG. 4), wherein clamp member 58 is in juxtaposed alignment with blade member 90. Clamp member 58 is moved between the open position and the closed position in response to actuation of clamp trigger 26 (FIG. 1).

Referring again to FIG. 2, outer tube 66 is slidably repositionable between an advanced position and a retracted position. Upon movement of outer tube 66 from the advanced position to the retracted position, clamp member 58 is moved from the open position (FIG. 3) to the closed position (FIG. 4). A proximal end of outer tube 66 includes an elongated slot 70 (FIG. 2) which receives projections (not shown) of rotatable nozzle 22 (FIG. 1) such that outer tube 66 is rotatably secured to, but slidable about, the projections to facilitate movement of outer tube 66 between the advanced and retracted positions.

The proximal end of outer tube 66 includes a bifurcated portion that defines an axially extending throughbore 72 that slidably receives wings 48 of torque adapter 46. A pair of diametrically opposed windows 74 are formed in the proximal end of outer tube 66. Windows 74 receive bosses (not shown) formed in handle assembly 12 (FIG. 1) to couple outer tube 66 to handle assembly 12 (FIG. 1).

Figure 6A:
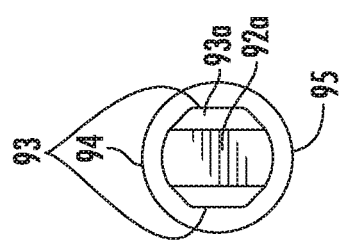
FIGS. 6A-G are front views of the blades of FIGS. 5A-G, respectively, in accordance with the present disclosure.
Figure 5A:
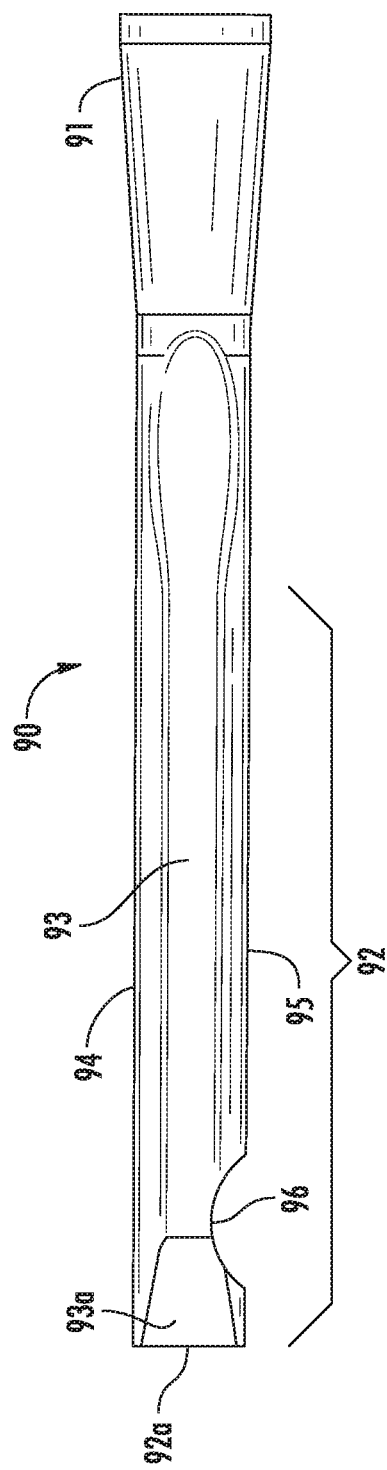
FIGS. 5A-G are side views of various embodiments of a blade of the surgical instrument of FIG. 1 in accordance with the present disclosure.

With reference to FIGS. 5A and 6A, blade 90 defines a longitudinal axis and includes a proximal portion 91 and a distal portion 92. Proximal portion 91 is configured to couple to waveguide 30. In embodiments, proximal portion 91 may be generally conical and may taper down to distal portion 92. Distal portion 92 includes a planar distal tip 92a, planar side segments 93, an arcuate top portion 94, an arcuate bottom portion 95, and a notch 96. Side segments 93 are substantially flat parallel to the longitudinal axis of blade 90. Side segments 93 include flat tapered segments 93a near distal tip 92a such that tapered segments 93a form a flat surface at distal tip 92a. Side segments 93 and/or tapered segments 93a may be configured to score or seal tissue as described in detail below. In embodiments, top portion 94 and bottom portion 95 may be generally arcuate. In some embodiments, top and bottom portions may have a common center of curvature. Notch 96 is disposed on bottom portion 95 and is configured to cut or dissect tissue as described in detail below. Notch 96 has a generally arcuate shape as shown in FIG. 5A. Top portion 94 contacts clamp member 58 when clamp member 58 is in the closed position. In some embodiments, top portion 94 may be configured to conform to the surface of clamp member 58.

In use, blade 90 may be used to dissect and seal tissue. During operation, TAG 20 is activated to ultrasonically translate or oscillate blade 90 along the longitudinal axis. As blade 90 oscillates, the temperature of blade 90 increases. When the temperature of blade 90 reaches a desired temperature, distal portion 92 of blade 90 may be used to dissect and/or seal tissue. The cutting properties of distal portion 92 are improved as the temperature of distal portion 92 increases. It is envisioned that any portion of distal portion 92 may be used to dissect tissue. In embodiments, notch 96 of distal portion 92 may be used to improve cutting properties of distal portion 92. Notch 92 may increase tissue contact or tissue tension during a cutting or back scoring motion to improve the cutting properties of bottom portion 95. In some embodiments, clamp member 58 may be used to increase the tension in tissue clamped between clamp member 58 and top portion 94 of blade 90.

When the temperature of blade 90 is increased, as described above, planar surfaces, e.g., side segments 93 of distal portion 92 of blade 90 may also be used to score or seal tissue. In embodiments, side segments 93 may seal tissue when the temperature of distal portion 92 is at or above 250° C. However, it is also envisioned that side segments 93 may seal tissue at temperatures below 250° C. by applying additional pressure to the tissue to be sealed against side segments 93, e.g., it has been shown that tissue may be sealed at a temperature as low as 90° C. Top portion 94 of blade 90 may be used to seal tissue. Clamp member 58 may apply additional pressure to the tissue to be sealed against top portion 94.

The ultrasonic motion of blade 90 results in decreasing internal stress from the proximal portion 91 to distal tip 92a. Thus, location of notch 96 is based on reducing physical strain and/or stress on the blade 90. In embodiments, if notch 96 is disposed too proximally, the reduction in the cross-sectional area as well as the stress concentration of notch 96 may result in excessive stress causing fracture of blade 90.

Figure 5B:
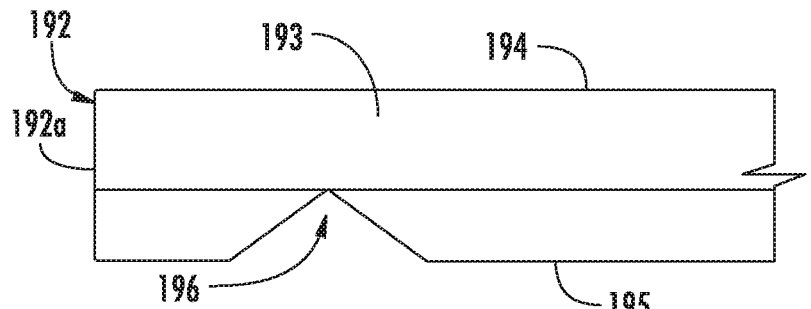
Figure 6B:
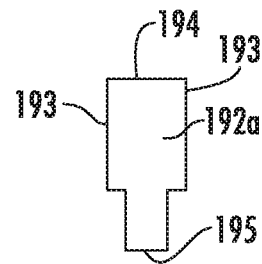

Referring to FIGS. 5B and 6B, another exemplary embodiment of a distal portion 192 in accordance with the present disclosure is shown. Distal portion 192 includes a planar distal tip 192a, planar side segments 193, a planar top portion 194, a planar bottom portion 195, and a triangular notch 196 disposed on bottom portion 195. Distal portion 192 is similar to distal portion 92 described above, as such only the differences are described in detail below for reasons of brevity. Bottom portion 195 has a stepped configuration as shown in FIG. 6B such that the bottom planar surface of bottom portion 195 is smaller than the planar surface of top portion 194, e.g., in a plane parallel to the longitudinal axis. In embodiments, tip 192a, side segments 193, top portion 194, and bottom portion 195 are configured to seal tissue as described above. In addition, tip 192a, side segments 193, top portion 194, bottom portion 195, and notch 196 are configured to dissect tissue as described above.

Figure 5C:
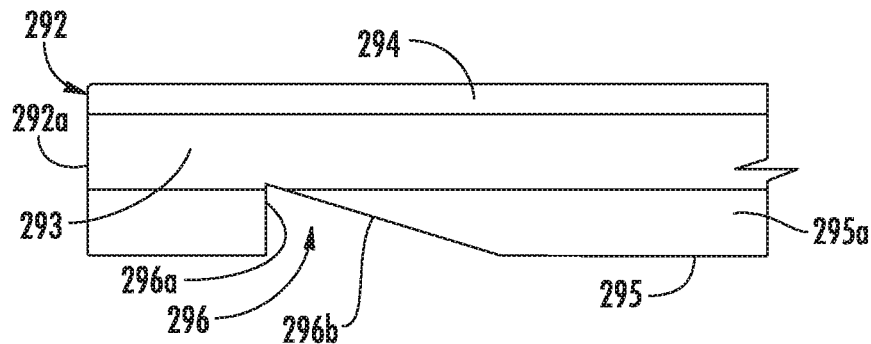
Figure 6C:
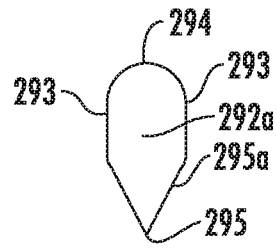

Referring to FIGS. 5C and 6C, yet another exemplary embodiment of a distal portion 292 in accordance with the present disclosure is shown. Distal portion 292 includes a planar distal tip 292a, planar side segments 293, an arcuate top portion 294, a pointed bottom portion 295, and a notch 296. Distal portion 292 is similar to distal portion 92 described above, as such only the differences will be described in detail below for reasons of brevity. Bottom portion 295 includes planar surfaces 295a that converge to form a pointed edge. In some embodiments, the pointed edge at the convergence of planar surfaces 295a is sharpened to improve the cutting properties of bottom portion 295a. Notch 296 includes a vertical distal surface 296a and an angled planar surface 296b. Vertical distal surface 296a of notch 296 may also be sharpened to improve the cutting properties of notch 296. In this embodiment, tip 292a, side segments 293, top portion 294, and planar surfaces 295a of bottom portion 295 are configured to seal tissue as described above. In addition, tip 292a, side segments 293, top portion 294, bottom portion 295, and notch 296 are configured to dissect tissue as described above.

Figure 5D:
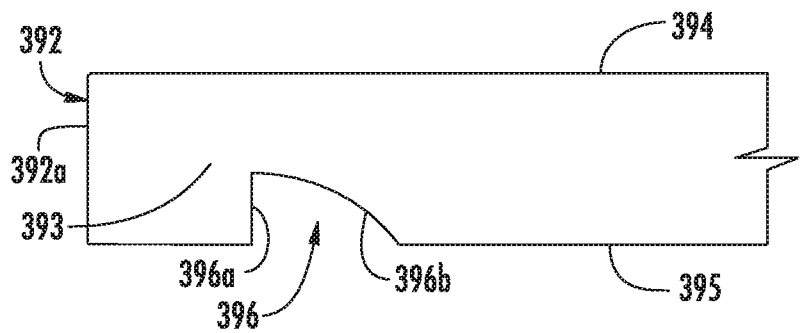
Figure 6D:
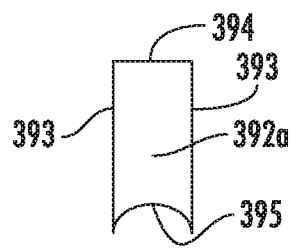

Referring to FIGS. 5D and 6D, still another exemplary embodiment of a distal portion 392 in accordance with the present disclosure is shown. Distal portion 392 includes a planar distal tip 392a, planar side segments 393, a planar top portion 394, a concave bottom portion 395, and a notch 396. Distal portion 392 is similar to distal portion 92 described above, as such only the differences will be described in detail below for reasons of brevity. Concave bottom portion 395 may be generally arcuate, which improves the cutting properties of distal portion 392 along bottom portion 395 between side segments 393. Notch 396 includes a vertical distal surface 396a and an arcuate surface 396b extending proximally therefrom. Vertical distal surface 396a may be sharpened to improve the cutting properties of notch 396. In this embodiment, tip 392a, side segments 393, and top portion 394 are configured to seal tissue as described above. In addition, tip 392a, side segments 393, top portion 394, bottom portion 395, and notch 396 are configured to dissect tissue as described above.

Figure 5E:
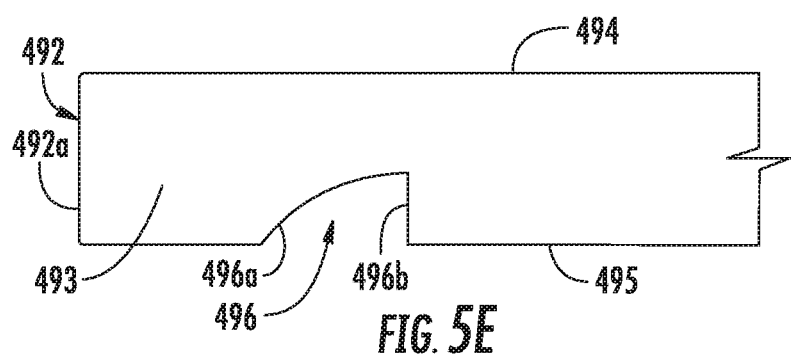
Figure 6E:
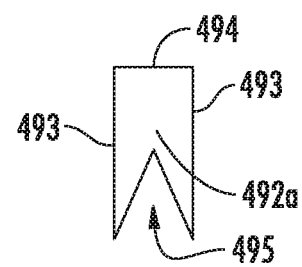

Referring to FIGS. 5E and 6E, still yet another exemplary embodiment of a distal portion 492 in accordance with the present disclosure is shown. Distal portion 492 includes a planar distal tip 492a, planar side segments 493, a planar top portion 494, a recessed bottom portion 495, and a notch 496. Distal portion 492 is similar to distal portion 92 described above, as such only the differences will be described in detail below for reasons of brevity. Recessed bottom portion 495 includes inwardly converging angled planar surfaces. The recess of bottom portion 495 may improve the cutting properties of distal portion 492 along bottom portion 495 between side segments 493. Notch 496 includes an arcuate surface 496a and a vertical proximal surface 496b. Vertical proximal surface 496b may be sharpened to improve the cutting properties of notch 496. In this embodiment, tip 492a, side segments 493, and top portion 494 are configured to seal tissue as described above. In addition, tip 492a, side segments 493, top portion 494, bottom portion 495, and notch 496 are configured to dissect tissue as described above.

Figure 5F:
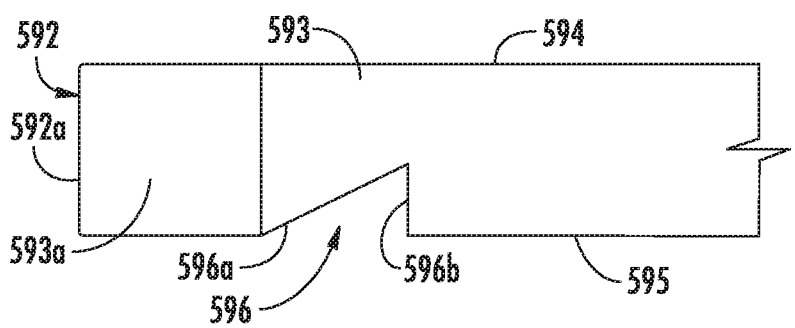
Figure 6F:
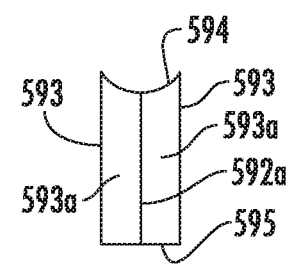

Referring to FIGS. 5F and 6F, another exemplary embodiment of a distal portion 592 in accordance with the present disclosure is shown. Distal portion 592 includes a pointed distal tip 592a, planar side segments 593, a concave top portion 594, a planar bottom portion 595, and a notch 596. Distal portion 592 is similar to distal portion 92 described above, as such only the differences will be described in detail below for reasons of brevity. Pointed distal tip 592a may be sharpened to improve the cutting properties of distal tip 592a. Concave top portion 594 is generally arcuate, which improves the cutting properties of distal portion 592 along top portion 594 between side segments 593. Notch 596 includes an angled surface 596a and a vertical proximal surface 596b. Vertical proximal surface 596b may be sharpened to improve the cutting properties of notch 596. In this embodiment, side segments 593, tapered segments 593a, and bottom portion 595 are configured to seal tissue as described above. In addition, tip 592a, side segments 593, tapered segments, 593a, top portion 594, bottom portion 595, and notch 596 are configured to dissect tissue as described above.

Figure 5G:
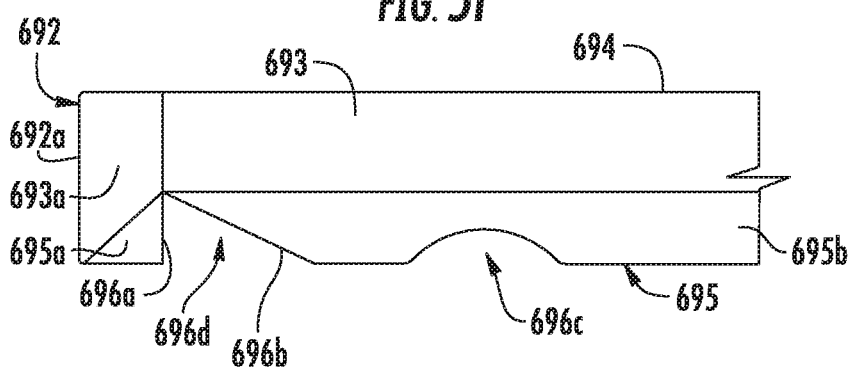
Figure 6G:
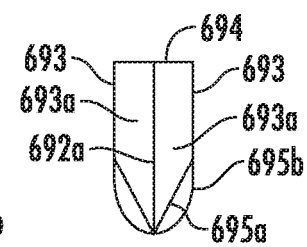

Referring to FIGS. 5G and 6G, yet another exemplary embodiment of a distal portion 692 in accordance with the present disclosure is shown. Distal portion 692 includes a pointed distal tip 692a, planar side segments 693, a planar top portion 694, a bottom portion 695, a proximal notch 696c, and a distal notch 696d. Distal portion 692 is similar to distal portion 92 described above, as such only the differences will be described in detail below for reasons of brevity. Pointed distal tip 692a may be sharpened to improve the cutting properties thereof.

As shown in FIG. 6G, bottom portion 695 includes planar surfaces 695a and an arcuate surface 695b. Planar surfaces 695a converge to form a pointed tip. In some embodiments, the pointed tip at the convergence of planar surfaces 695a may be sharpened to improve the cutting properties of a portion of bottom portion 695. Arcuate surface 695b is positioned proximal to planar surfaces 695a. In embodiments, arcuate surface 695b may be positioned proximal to planar surfaces 695a. Proximal notch 696c is generally arcuate and distal notch 696d includes a vertical distal surface 696a and an angled planar surface 696b. Vertical distal surface 696a may be sharpened to improve the cutting properties of distal notch 696d. It is envisioned that any of the notches described above may be used in place of either of notches 696c, 696d. In this embodiment, side segments 693, tapered segments 693a, top portion 694, and planar surfaces 695a of bottom portion 695 are configured to seal tissue as described above. In addition, tip 692a, side segments 693, tapered segments, 693a, top portion 694, bottom portion 695, and notches 696c, 696d are configured to dissect tissue as described above.

Distal portions 192, 292, 392, 492, 592, and 692 are used in a manner substantially similar to distal portion 92 described above, as such the use of these distal portions will not be discussed in detail.

Although various embodiments of distal portions have been described in detail above, it is envisioned that a distal portion may include any combination of features as described above. It is also envisioned that a distal portion may include more than two notches. Moreover, while particular elements of distal portions have been described as configured to seal and/or dissecting tissue, this is not meant to be limiting to the capabilities of these or other elements described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A tool assembly comprising:
   an ultrasonic blade defining a longitudinal axis and including a proximal portion and a distal portion, the distal portion including:
     a top surface configured to seal tissue;
     a bottom surface having a notch defined therein, the notch first planar surface and a second planar surface that are in contact with each other and extend from the bottom surface towards the top surface, at least one of the first planar surface or the second planar surface configured to dissect tissue; and
     side segments extending between the top and bottom surfaces; and
   a jaw member configured to move relative to the ultrasonic blade and to contact the top surface.

2. The tool assembly according to claim 1, wherein the distal portion of the ultrasonic blade includes a planar distal tip.

3. The tool assembly according to claim 1, wherein the distal portion of the ultrasonic blade includes a pointed distal tip.

4. The tool assembly according to claim 1, wherein the bottom surface is formed at a convergence of two planar surfaces.

5. An ultrasonic surgical instrument, comprising:
   a handle assembly;
   an elongated body extending distally from the handle assembly, the elongated body defining a longitudinal axis and including a waveguide; and
   a tool assembly including a blade having a proximal portion and a distal portion, the proximal portion coupled to a distal end of the waveguide, the distal portion including:
     a top surface configured to seal tissue;
     a bottom surface having a notch defined therein, the notch first planar surface and a second planar surface that are in contact with each other and extend from the bottom surface towards the top surface, at least one of the first planar surface or the second planar surface configured to dissect tissue; and
     side segments extending between the top and bottom surfaces.

6. The ultrasonic surgical instrument according to claim 5, wherein tool assembly includes a jaw member moveable relative to the blade between an open position in which the jaw member is spaced from the blade and a closed position in which the jaw member is in juxtaposed alignment with the blade.

7. The ultrasonic surgical instrument according to claim 6, wherein the jaw member is configured to clamp tissue against a top portion the blade.

8. The ultrasonic surgical instrument according to claim 5, wherein the distal portion of the blade includes a planar distal tip.

9. The ultrasonic surgical instrument according to claim 5, wherein the distal portion of the blade includes a pointed distal tip.

10. The ultrasonic surgical instrument according to claim 5, wherein the bottom surface is formed at a convergence of two planar surfaces.

\* \* \* \* \*